United States Patent [19]

Mars

[11] Patent Number: 5,201,702
[45] Date of Patent: Apr. 13, 1993

[54] BRACE FOR SUPPORTING THE HEAD IN AN UPRIGHT POSITION

[76] Inventor: Suzanne P. Mars, 23649 Duffield Rd., Shaker Hts., Ohio 44122

[21] Appl. No.: 510,126

[22] Filed: Apr. 17, 1990

[51] Int. Cl.$^5$ .............................................. A61F 5/01
[52] U.S. Cl. ....................................... 602/17; 602/18
[58] Field of Search ................................. 602/17, 18; 128/DIG. 23, 845

[56] References Cited

U.S. PATENT DOCUMENTS

| | | | |
|---|---|---|---|
| 2,796,866 | 6/1957 | Cohen | 602/17 X |
| 3,724,452 | 4/1973 | Nitschke | 602/18 |
| 3,957,040 | 5/1976 | Calabrese | 602/17 X |
| 4,161,946 | 7/1979 | Zuesse | 602/17 X |
| 4,383,523 | 5/1983 | Schurman | 602/17 X |
| 5,003,968 | 4/1991 | Mars | 602/17 |

Primary Examiner—Richard J. Apley
Assistant Examiner—Linda C. M. Dvorak
Attorney, Agent, or Firm—Weston, Hurd, Fallon, Paisley & Howley

[57] ABSTRACT

An apparatus is provided for supporting the head, the neck and the upper body. The apparatus includes a first assembly for supporting an upper portion of the head. In one preferred example, the first support assembly includes a headband to be fitted around the head for reducing lateral-rotational movements due to bio-mechanical thrust. A second support assembly is provided for supporting a lower portion of the head. In a preferred example, the second support assembly includes a chin support which is structurally separate from the first support assembly. A third support assembly is provided for supporting a portion of the upper body. In a preferred example, the third support assembly includes a vest which substantially encompasses the upper body. An interconnecting arrangement is employed to adjustably and detachably connect the first support assembly and the second support assembly to portions of the third support assembly. The first support assembly, the second support assembly, and the third support assembly can be used to significantly reduce bio-mechanical thrust and, in one example, maintain the head in a substantially upright position.

19 Claims, 4 Drawing Sheets

BRACE FOR SUPPORTING THE HEAD IN AN UPRIGHT POSITION

BACKGROUND OF THE INVENTION

1. Field of the Invention.

The present invention relates to an apparatus for counteracting bio-mechanical thrust, and more particularly to a device that keeps the head in an upright position.

2. Description of the Prior Art.

As is known, the human head is a relatively heavy object, and without proper neuro-muscular control, the head is difficult to maintain in an upright position. Those persons referred to as "spastic" have lost just such control. Losing the ability to maintain the head in an upright position causes slumping or biomechanical thrusting of the head and/or upper body in spastic persons. Bio-mechanical thrusting is disadvantageous for several reasons. First, when the head is slumped, the trachia can be compressed, thus inhibiting breathing. Second, bio-mechanical thrusting makes eating difficult. To facilitate eating, many spastic people must either be fed by another or eat in a reclined position. The first option can be expensive and demeaning, while the second option can be dangerous since eating while inclined can lead to choking.

Third, a slumped head leads to problems with psycho-socio behavior patterns. That is loss of eye contact with others not only interferes with the spastic person's ability to learn, but also leads to a feeling of isolation. Finally, bio-mechanical thrusting promotes skeletal deformity throughout, among other regions, the upper back and neck.

There are at least two techniques presently employed to support the head, neck and/or upper body. In one technique, the neck and head are "immobilized" by, for example, a "halo" brace, which actually interconnects the skull with the brace. Immobilization, which prohibits substantially all movement of the spastic person, has been found to promote, rather than alleviate, spasticity. To reduce the spasticity due to immobilization, drugs are applied to relax the muscles of the spastic person. Accordingly, during immobilization, the spastic person's muscles become flaccid.

In another technique known as "stabilization," the spastic person is allowed some movement. While immobilization may be necessary in some cases, for less severe cases, stabilization is preferred. The stabilization can be achieved through use of one or more braces applied to either the neck, head and/or upper body. It is believed that stablization techniques employed to date are highly deficient.

Designers of braces employed for stabilization have failed to appreciate that bio-mechanical thrust is not halted by bracing just one or two portions of the body. It is believed necessary to counteract interior/posterior, lateral and rotational movements to which the neck and head, as well as the upper body, are subjected. Indeed, there is a need for a simple, yet effective brace that provides support to each part of the bod subjected to one or more of these movements. The ideal brace would allow for little movement, but effectively balance all of the forces generated by bio-mechanical thrust.

SUMMARY OF THE INVENTION

According to the present invention, an apparatus for maintaining the head in an upright position is provided. The apparatus includes first support means for supporting an upper portion of the head. Second support means are provided for supporting a lower portion of the head, a portion of the second support means is preferably disposed proximate to the chin. Third support means are provided for supporting the upper body. The third support means encompasses a substantial portion of the upper body. Interconnecting means are employed to adjustably and detachably connect the first support means and the second support means to portions of the third support means. Accordingly, biomechanical thrust is significantly reduced and the head can be held in a substantially upright position.

In the preferred embodiment, the first support means includes a padded plate conforming to the back of the head to which a detachable flexible headband is operatively connected. A portion of the interconnecting means is employed to adjustably couple the plate to the third support means, which is preferably a vest that can be adjustably and detachably fastened proximate to the lower thorax of the user. In the preferred embodiment of the present invention, the second support means is a chin support which is structurally separate from the first support means and is adjustably and detachably connected to the vest. The chin support may be supported by two spaced elongate members which serve to further distribute force throughout the second and third support means.

Numerous advantages will be appreciated by those skilled in the art.

One advantage of the present invention is that it represents a simple, yet comprehensive solution for spastic persons who are afflicted by bio-mechanical thrust. In particular, the design is exceedingly flexible and allows for a wide range of adjustment in the first, second and third support means. Moreover, the brace is functional and compact so that the brace is easier to use and wear than many stabilization-type braces commonly encountered. Finally, the brace of the present invention is designed to be lightweight and comfortable so that the user is not made to feel aware of its presence.

Another advantage of the present invention is that it possesses a superior construction. More specifically, due to the modularity of the brace there is some movement among all the parts. Such movement at least reduces the possibility that the spastic person will have an adverse reaction to using the brace. The movement among the first, second and third support means also provides a means for dissipating force throughout the brace. Additionally, the brace is aesthetically pleasing in appearance and inevitably promotes the self esteem of the user. It is equally important that the construction of the brace allows the user to perform normal functions such as eating and breathing as well as promotes productive psycho-socio behavior as a result of maintaining the head in the upright position.

Yet another advantage of the present invention is that it is easy to manufacture and economical. More specifically, the components used to build the brace are readily fabricated and are therefore cost-effective to produce. The design is uncomplicated and, at the same time, the components can be made from materials that are durable and wear resistant. Due to the modularity of the brace, it can be easily shipped in a disassembled state and readily assembled at its point of use or sale.

These and other features, advantages and objects of the present invention will be further understood and appreciated by those skilled in the art by reference to the following written specification, claims and appended drawings,

DESCRIPTION OF THE PREFERRED EMBODIMENT

It is to be understood that the invention described below may assume various alternative orientations and step sequences except where expressly specified to the contrary. It is also to be understood that the specific devices and processes illustrated in the attached drawings, and described in the following specification, are simply exemplary embodiments of the inventive concepts defined in the appended claims. Hence, specific dimensions, and other physical characteristics related to the embodiments disclosed herein are not to be considered as limiting, unless the claims by their language expressly state otherwise.

Figure 1:
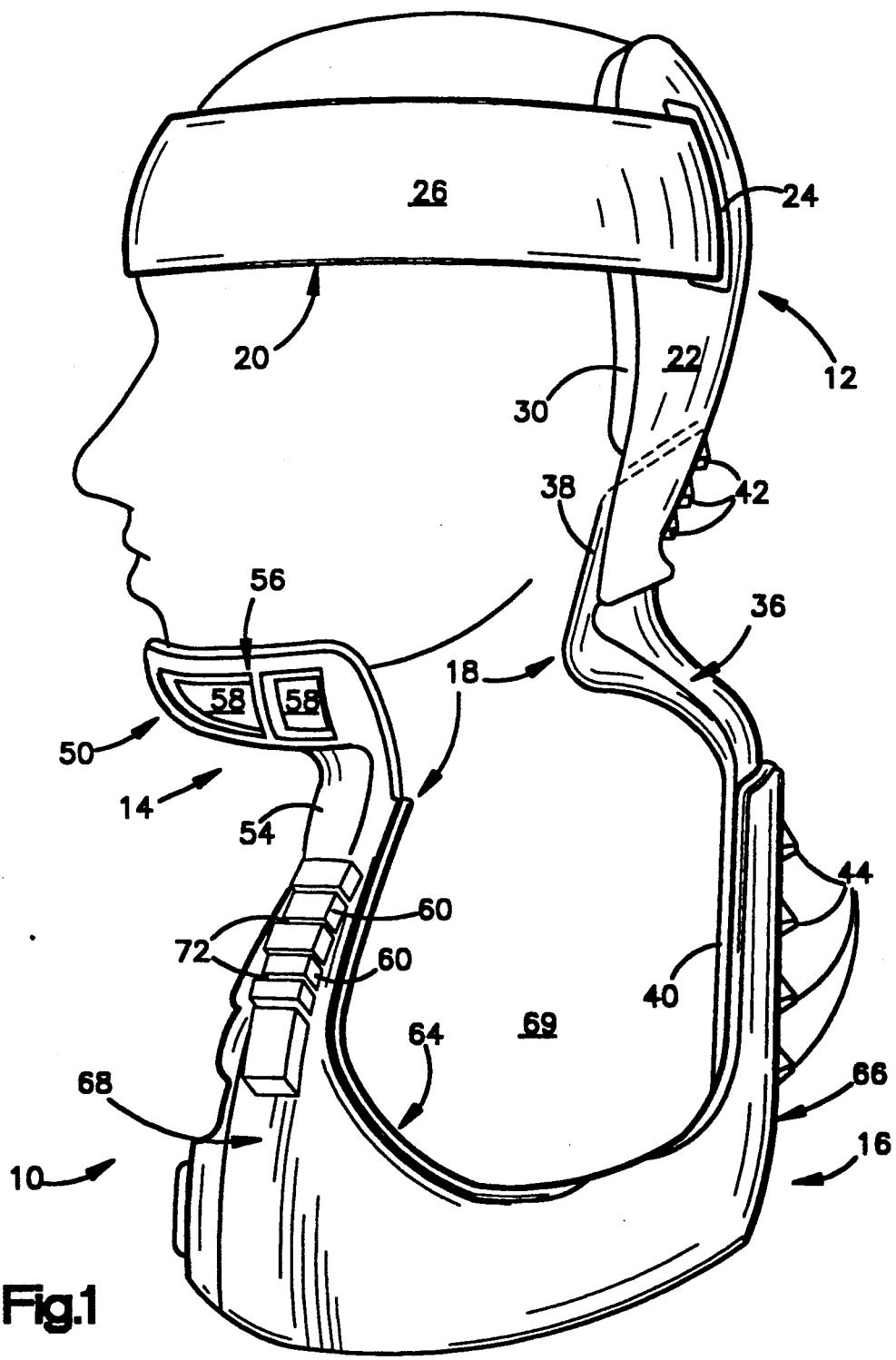
FIG. 1 is a side elevational view of the brace embodying the present invention.

Referring to FIG. 1, a brace for maintaining a head in an upright position is indicated by the numeral 10. The brace 10 includes first support means 12 for supporting an upper part of the head, second support means 14 for supporting a lower part of the head and third support means 16 for supporting a portion of the upper body. The first support means 12 and the second support means 14 are adjustably and detachably connected to the support means 16 by way of interconnecting means 18.

As can be appreciated, the brace 10 is typically used with spastic persons who are incapable of maintaining their heads in an upright position due primarily to biomechanical thrust. It is a specific object of the invention to significantly reduce anterior-posterior, lateral and rotational movements to which the spastic person is typically subjected. Spastic persons, however, are not the only group of people who can benefit from the use of brace 10. More particularly, as will be understood after the discussion below, race car drivers could advantageously use the brace 10 to avoid whiplash and other accident-related injuries since the brace 10 serves to stabilize the head, neck and upper body and thus counteract violent motion which is commonly generated as a result of high speed accidents.

The first support mean 12 includes a headband 20 which is operatively connected to a plate 22 (FIG. 2) which plate 20 includes a pair of slots disposed in an upper portion thereof. In the preferred embodiment, the headband 20 (FIG. 3) is defined by two flexible pieces 26 and 28, which may be a substantially elastic heavy cloth or the like, each of which extends through slots 24 and is secured to an inner surface of plate 22 by known fastening means such as glue, stapling, or the like. In one example, the pieces 26 and 28 are secured at end portions by VELCRO brand hook and loop fastening means 29. In alternative arrangements, other known fastening means could be employed.

Figure 2:
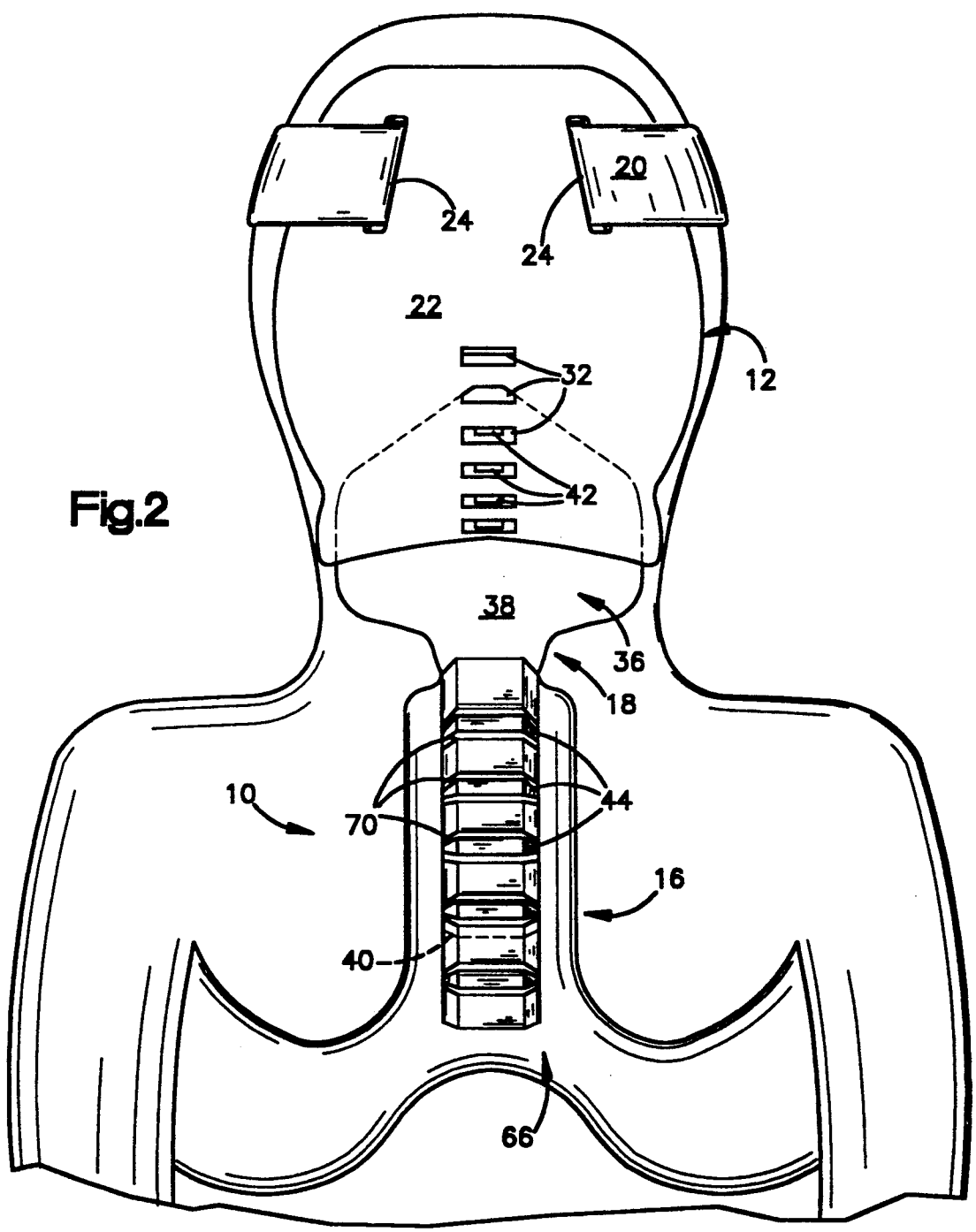
FIG. 2 is a rear elevational view of the brace.
Figure 3:
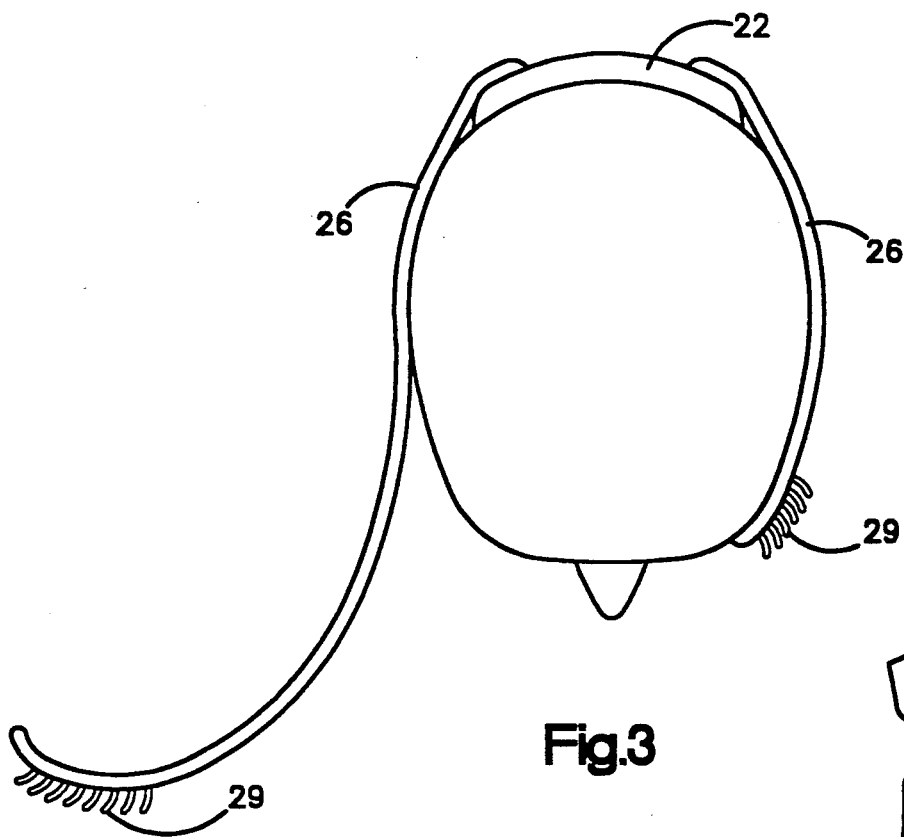
FIG. 3 is a partial top plan view of the brace, specifically illustrating a headband connected thereto.

The plate 22, as best illustrated in FIG. 2, has a shape conforming to the head and, in one example, is constructed from lightweight, molded plastics material such as polystyrene, ABS, or any other well-known plastics material commonly used for constructing braces. As will also be appreciated by those skilled in the art, other lightweight materials, such as aluminum, magnesium or the like, which would serve to provide a reasonable amount of rigid support, could be employed. Except where otherwise expressed to the contrary, all of the components used to construct brace 10 are relatively inexpensive, durable plastic, such as the kind discussed above. To provide further support for the back of the head, plate 22 (FIG. 1) is provided with a liner 30 which is preferably constructed from a soft, flexible synthetic material. The liner 30 is preferably mounted to an inner surface of the plate 22 by a conventional adhesive. Apertures 32 (FIG. 2) are also defined in a lower portion of plate 22, the significance of which apertures 32 will be discussed in further detail below.

The plate 22 (FIGS. 1 and 2) is adjustably and detachably connected to a back portion of the third support means 16 by way of a portion of interconnecting means 18. In one example, the interconnecting means 18 includes a first interconnecting member 36 having a first end 38 and a second end 40. In the preferred embodiment, a set of projections 42 and a set of projections 44 are disposed along the first end 38 and the second end 40.

Figure 4:
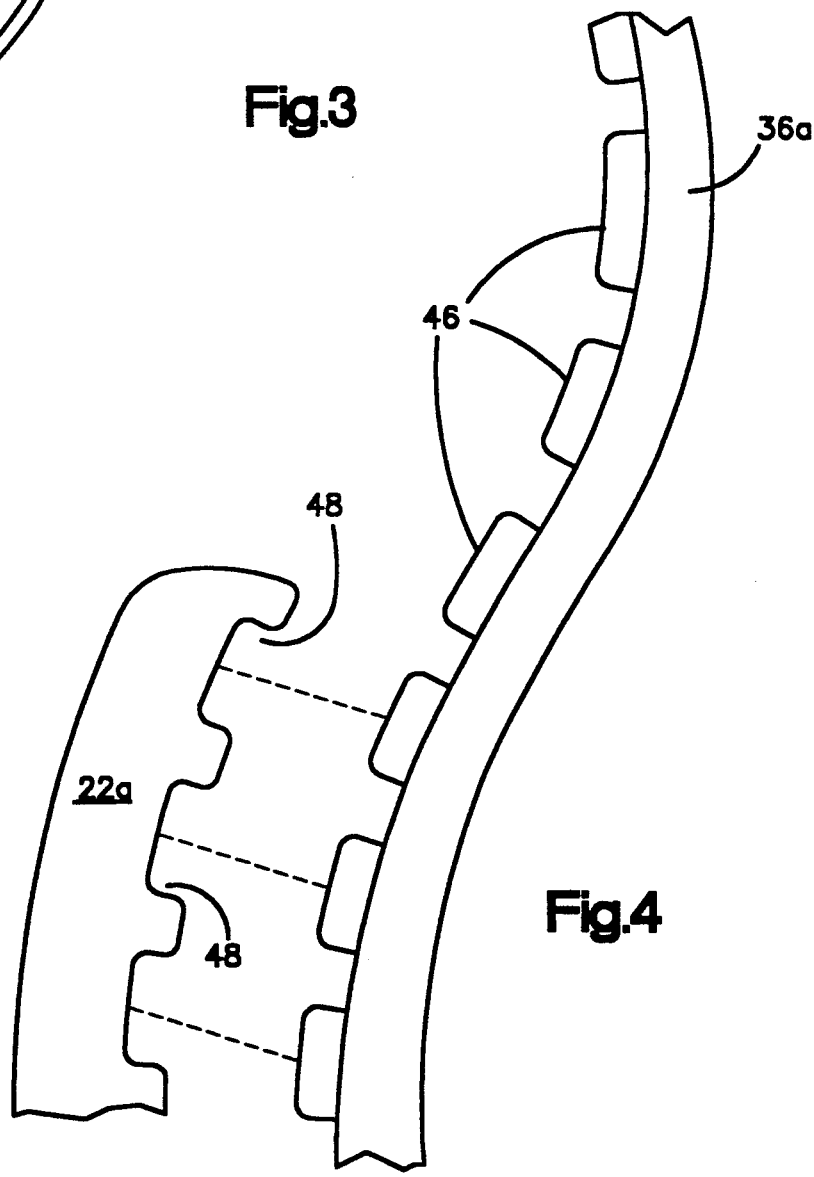
FIG. 4 is a side elevational view of an alternate embodiment of a fastening arrangement to be used with the brace.

Referring to FIG. 2, one or more of projections 42 are snap-fitted into apertures 32 to position the first end 38 of interconnecting member 36 relative to the plate 22. As can be noted, the height of the plate 22 is adjusted by the number of projections 42 that are fitted within apertures 32. Other arrangements for adjustably fastening first end 38 to plate 22 are contemplated by the present invention. For example, as illustrated in FIG. 4, resilient male members 46, which are configured on alternative interconnecting member 36a, are force fitted into female receptacles 48, which female receptacles 48 are configured along a lower portion of an alternative plate 22a.

Figure 5:
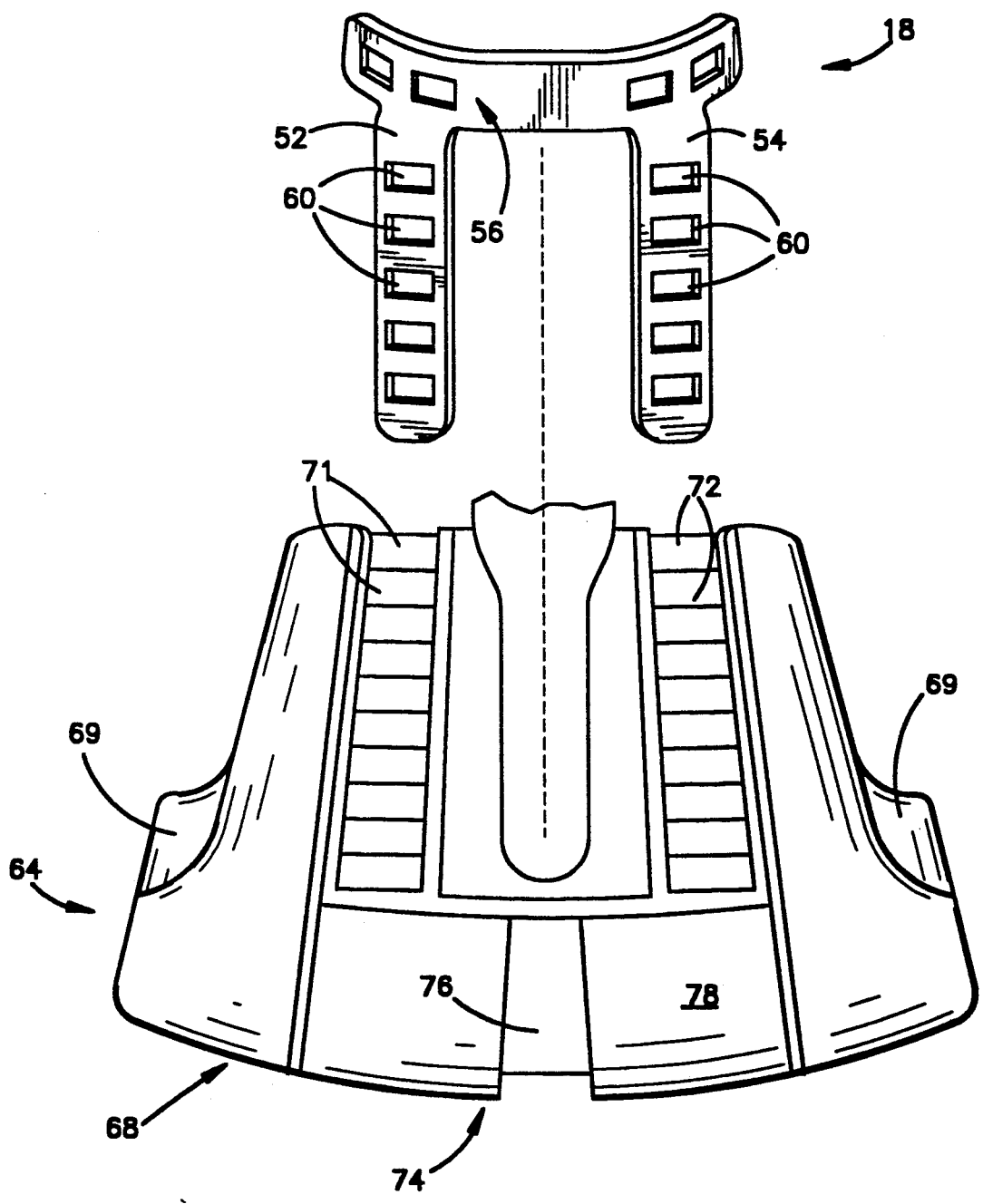
FIG. 5 is a broken-away, front elevational view of the brace, specifically illustrating a vest employed therewith.

Referring to FIGS. 1 and 5, the second support means 14 is illustrated in further detail. The second support means 14 includes a chin support 50 integrally connected to interconnecting members 52 and 54. The chin support 50 is configured into a frame 56 including one or more apertures 58 which allow the chin to breath during use of the second support means 14. While the apertures 58 are shown to be rectangular or square in FIG. 1, in the most preferred embodiment, they are round to facilitate comfort for the user. As with interconnecting member 36, interconnecting members 52, 54 include projections, which in FIGS. 1 and 5 are designated by the numeral 60. While the chin support 50 could be secured to the third support means 16 through employment of a single interconnecting member without impairing the operation of the brace 10, it has been found that the use of spaced interconnecting members 52 and 54 facilitates force distribution between the second support means 14 and the third support means 16.

Referring again to FIGS. 1-2 and 5, the third support means 16 preferably includes a vest 64 having a dorsal section 66 and a thoracic section 68. Additionally, the vest 64 includes arm apertures 69. As best illustrated in FIG. 2, the dorsal section 66 defines a plurality of apertures 70 for receiving one or more of projections 44. The number of projections 44 disposed within apertures 70 is dictated by the amount of adjustment desired between the second end 40 of interconnecting member 36 and dorsal section 66. As explained above, pursuant to a discussion of FIG. 4, the adjustable fastening arrangement between the second end 40 and the dorsal section 66 could be implemented with alternative fastening arrangements. As can now be appreciated, a maximum amount of design flexibility is provided between plate 22 and dorsal section 66. More specifically, adjustments are provided at ends 38 and 40 of interconnecting member 36 so that the position of first support means 12 can be optimally set with respect to the third support means 16.

Referring specifically to FIG. 5, the thoracic section 68 of vest 64 is illustrated in further detail. The thoracic section 68 is configured to include a first set of apertures 71 and a second set of apertures 72 in which the projections 60 of interconnecting members 52, 54 are received. As with the fastening arrangements discussed above, alternative arrangements could be employed to achieve the adjustable, detachable connection between interconnecting members 52, 54 and thoracic section 68.

The thoracic section 68 further includes fastening means 74. In the preferred embodiment, the fastening means 74 (FIG. 5) is implemented through use of a male-coupling member 76 snapfitted to female coupling member 78. When the user is wearing the vest, the fastening means 74 is disposed toward the lower portion of the thorax for convenient handling. In case of emergency, the vest 64 can be quickly shed by simply reaching down and decoupling the fastening means 74.

In the preferred form of operation (FIGS. 1-2 and 5), the brace 10 can be custom assembled for each user since it is constructed in modular form. Prior to use, the support means 12, 14 and 16, as well as the interconnecting means 18, are fitted together and various adjustments are made using apertures 32, and 70-72 in conjunction with projections 42, 44, and 60 to roughly configure the brace 10 for the particular dimensions and contour of the user. The vest 64 is then fitted around the upper body of the user so that the male coupling member 76 can be snapped into the female coupling member 78 and the first headband piece 26 can be secured to the second headband piece 28 by way of the VELCRO fastening means 29. Once the brace 10 is applied to the user, secondary adjustments can be made, particularly using adjustable connections defined by apertures 32, and 71-72 and projections 42, 60.

An exceedingly advantageous brace 10 is provided for use by spastic persons. Since the brace 10 is modular, there is "give" or "play" between the components, i.e. support means 12, 14 and 16 as well as interconnecting means 18. This give in the components not only eliminates problems commonly encountered with immobilization techniques, but further enhances forced distribution throughout the brace 10.

Additionally, brace 10 is adjustable at a plurality of points defined along the brace 10. More specifically, adjustment is possible for portions ranging from an upper portion of the head all the way down to the bottom of the thorax. Consequently, the brace can be advantageously custom fitted for users of all different shapes and sizes.

Finally, the brace comprehensively addresses the problems of bio-mechanical thrust. That is, total support is provided for the entire head and the entire upper part of the body. Even more specifically, posterior-anterior, lateral and rotational movements are totally balanced by the brace 10 so that movements commonly generated throughout the upper half of the body as well as the neck and head are totally stabilized. For example, by using the headband 20 in conjunction with the plate 22 and the chin support 50, accommodation is provided for each of the above-mentioned movements with respect to the head. Additionally, the vest 64 accommodates for each of the movements with respect to the upper body. As can now be appreciated, the brace 10 approaches the problem of bio-mechanical thrust in holistic terms and allows for a solution that is believed to have not been heretofore appreciated.

In the foregoing description, it will be readily appreciated by those skilled in the art that modifications may be made to the invention without departing from the concepts disclosed herein. Such modifications are to be considered as included in the following claims unless those claims, by their language, expressly state otherwise.

What is claimed is:

1. An apparatus for supporting the head, the neck, and the upper body, the apparatus comprising:
    first support means for supporting an upper portion of the head;
    second support means for supporting a lower portion of the head, a portion of the second support means being disposed proximate to the chin;
    third support means for supporting a portion of the upper body, the third support means including a front portion and a rear portion, said front and rear portions cooperating to encompass a substantial portion of the upper body;
    first interconnecting means for detachably connecting the first support means to the rear portion of the third support means;
    second interconnecting means for detachably connecting the second support means to the front portion the third support means; and
    whereby the first support means, the second support means, and the third support means cooperatively function to significantly reduce bio-mechanical thrust and to allow for maintenance of the head in a substantially upright position.

2. The apparatus of claim 1, wherein the first support means includes a headband encompassing a substantial portion of the upper head, whereby lateral-rotational movements due to biomechanical thrust are significantly reduced.

3. The apparatus of claim 2, wherein the headband is substantially elastic.

4. The apparatus of claim 2, wherein the headband includes two pieces, each of which has an end, and wherein hook and loop fastening means are disposed on the ends to allow for detachable coupling of the ends.

5. The apparatus of claim 1, wherein the first support means is structurally separate from the second support means.

6. The apparatus of claim 1, wherein the third support means includes a vest having detachable fastening means, and wherein the detachable fastening means are disposed near the front of the user's body when the apparatus is being employed.

7. The apparatus of claim 6, wherein the detachable fastening means is adjustable.

8. The apparatus of claim 1, wherein the second support means includes a chin support.

9. The apparatus of claim 8, wherein:

the second interconnecting means includes a first interconnecting member having a first end and a second end; and the first end of the first interconnecting member is connected to the chin support and the second end of the first interconnecting member is detachably connected to the third support means.

10. The apparatus of claim 9, wherein the first interconnecting member and the third support means are adapted to allow for positional adjustment between the second end of the first interconnecting member and the third support means.

11. The apparatus of claim 9, wherein:

the second interconnecting means includes a second interconnecting member having a first end and a second end;

the first end of the second interconnecting member is connected to the chin support and the second end of the second interconnecting member is detachably connected to the third support means; and the first and second interconnecting members are spaced from one another to thereby distribute biomechanical thrust generated by the user.

12. The apparatus of claim 2, wherein:

the first support means includes a plate conforming to the head and operatively connected to the headband;

the first interconnecting means includes a third interconnecting member having a first end and a second end; and the first end of the third interconnecting member is detachably connected to the plate and the second end of the third interconnecting member is detachably coupled to the third support means.

13. The apparatus of claim 12, wherein the plate and the third interconnecting member are adapted to allow for positional adjustment between the first end of the third interconnecting member and the plate.

14. The apparatus of claim 12, wherein the third interconnecting member and the third support means are adapted to allow for positional adjustment between the second end of the third interconnecting member and the third support means.

15. An apparatus for supporting the head, the neck and the upper body, the apparatus comprising:

first support means for supporting an upper portion of the head, the first support means including a headband encompassing a substantial portion of the upper head;

second support means for supporting a lower portion of the head, the second support means including a chin support, the second support means being structurally separate from the first support means;

a vest having detachable fastening means;

a first interconnecting member for operatively connecting the chin support to a front portion of the vest;

a second interconnecting member for operatively connecting the first support means to a rear portion of the vest; and whereby the first support means, the second support means and the vest cooperatively function to significantly reduce biomechanical thrust and maintain the head in a substantially upright position.

16. A method for supporting the head, the neck and the upper body, the method comprising:

providing first support means;

supporting an upper portion of the head using the first support means;

providing second support means;

supporting a lower portion of the head using the second support means, the second support means being disposed proximate to the chin;

providing third support means;

encompassing a substantial portion of the upper body with the third support means;

supporting a portion of the upper body using the third support means;

providing first and second interconnecting means; and detachably connecting the first support means and the second support means to rear and front portions of the third support means using the first and second interconnecting means, respectively.

17. The method of claim 16, wherein the first support means includes means for reducing lateral-rotational movements of the head due to bio-mechanical thrust.

18. The method of claim 16, further comprising the step of vertically adjusting the position of the first support means relative to the third support means.

19. The method of claim 16, further comprising the step of vertically adjusting the position of the second support means relative to the third support means.

* * * * *